(12) United States Patent
Barbot et al.

(10) Patent No.: US 12,102,307 B2
(45) Date of Patent: *Oct. 1, 2024

(54) SURGICAL DELIVERY DEVICES, SYSTEMS, AND METHODS

(71) Applicant: Vita Group, LLC, Woodbury, MN (US)

(72) Inventors: Justin Barbot, Dunseith, ND (US); Richard Arthur Thompson, II, St. Louis Park, MN (US); Thomas Arthur Tedham, Eden Prairie, MN (US); Reed Oliver Saunders, Minneapolis, MN (US)

(73) Assignee: Vita Group, LLC, Woodbury, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/832,814

(22) Filed: Jun. 6, 2022

(65) Prior Publication Data

US 2022/0296226 A1    Sep. 22, 2022

Related U.S. Application Data

(63) Continuation of application No. 17/519,039, filed on Nov. 4, 2021, now Pat. No. 11,350,917, which is a continuation of application No. 17/518,090, filed on Nov. 3, 2021, now Pat. No. 11,364,023, which is a continuation of application No. 17/092,017, filed on Nov. 6, 2020.

(51) Int. Cl.
*A61B 17/00* (2006.01)

(52) U.S. Cl.
CPC ............ *A61B 17/00234* (2013.01); *A61B 2017/00362* (2013.01); *A61B 2017/00871* (2013.01)

(58) Field of Classification Search
CPC .... A61B 17/00234; A61B 2017/00362; A61B 2017/00871; A61F 2/12; A61F 2230/0026; A61F 2230/0067; A61F 2250/0071; A61F 2250/0097
See application file for complete search history.

(56) References Cited

U.S. PATENT DOCUMENTS

| | | | |
|---|---|---|---|
| 3,111,943 | A | 11/1963 | Orndorff |
| 3,448,915 | A | 6/1969 | Schwarzkopf |
| 3,556,389 | A | 1/1971 | Gregoire |
| 5,052,554 | A | 10/1991 | Leonard |
| 5,228,234 | A | 6/1993 | de Klerk et al. |
| 7,351,196 | B2 | 4/2008 | Goldmann et al. |
| 7,494,495 | B2 | 2/2009 | Delorme et al. |
| 8,322,926 | B2 | 12/2012 | Ejeblad |

(Continued)

OTHER PUBLICATIONS

Keller Medical Inc., "Instructions for Use, Keller Funnel 2, HA-005," Keller Medical, Inc., May 2019, 2 pages.

(Continued)

*Primary Examiner* — Mohamed G Gabr
(74) *Attorney, Agent, or Firm* — Fish & Richardson P.C.

(57) ABSTRACT

A device for delivering an implant to a surgical location of a patient is provided. In some embodiments, an example device includes a polymer body having first and second tapered sections and a sealed cavity defined by the polymer body. The polymer body is separable between the first and second tapered sections.

18 Claims, 7 Drawing Sheets

(56) References Cited

U.S. PATENT DOCUMENTS

| | | | |
|---|---|---|---|
| 8,939,886 | B2 | 1/2015 | Chu |
| D738,490 | S | 9/2015 | Anderson |
| D752,739 | S | 3/2016 | Anderson |
| 9,474,593 | B2 | 10/2016 | Anderson |
| D773,652 | S | 12/2016 | Anderson |
| D775,725 | S | 1/2017 | Anderson |
| D776,806 | S | 1/2017 | Anderson |
| 9,615,908 | B2 | 4/2017 | Anderson |
| 9,730,728 | B2 | 8/2017 | Anderson |
| 9,808,284 | B2 | 11/2017 | Anderson |
| 9,925,028 | B1 | 3/2018 | Rosenberg |
| 10,058,415 | B2 | 8/2018 | Preissman |
| 10,092,385 | B2 | 10/2018 | Anderson |
| 10,575,936 | B2 | 3/2020 | Rosenberg |
| 10,939,985 | B2 | 3/2021 | Winn |
| 11,350,917 | B2 | 6/2022 | Barbot et al. |
| 11,364,023 | B2 * | 6/2022 | Barbot ............. A61B 17/00234 |
| 11,452,511 | B2 | 9/2022 | Barbot et al. |
| 2007/0276484 | A1 | 11/2007 | Abell et al. |
| 2008/0221386 | A1 * | 9/2008 | Gellman .......... A61B 17/06109 600/37 |
| 2008/0250256 | A1 | 10/2008 | Hagiwara |
| 2009/0204107 | A1 | 8/2009 | Keller et al. |
| 2010/0278460 | A1 | 11/2010 | Ejeblad |
| 2010/0280610 | A1 * | 11/2010 | Preissman ................. A61F 2/12 623/8 |
| 2011/0144417 | A1 | 6/2011 | Jagger et al. |
| 2011/0144422 | A1 * | 6/2011 | Chu ..................... A61F 2/0045 600/37 |
| 2012/0143331 | A1 | 6/2012 | Keller et al. |
| 2014/0074235 | A1 | 3/2014 | Keller et al. |
| 2015/0126812 | A1 | 5/2015 | Anderson |
| 2016/0302914 | A1 | 10/2016 | Keller et al. |
| 2016/0374720 | A1 | 12/2016 | Anderson et al. |
| 2018/0116779 | A1 | 5/2018 | Marx |
| 2018/0161148 | A1 | 6/2018 | Keller et al. |
| 2019/0117365 | A1 * | 4/2019 | Winn ................. A61B 17/3468 |
| 2019/0321606 | A1 | 10/2019 | Lenihan et al. |
| 2020/0276005 | A1 | 9/2020 | Sufyan et al. |
| 2022/0142625 | A1 | 5/2022 | Barbot et al. |
| 2022/0142627 | A1 | 5/2022 | Barbot et al. |
| 2022/0142628 | A1 | 5/2022 | Barbot et al. |
| 2022/0142764 | A1 | 5/2022 | Barbot et al. |

OTHER PUBLICATIONS

KellerFunnel.com, "Keller Funnel 2, Frequently Asked Questions," May 2019, retrieved Jan. 13, 2021 from URL <https://www.kellerfunnel.com/faq>, 4 pages.

Panczel et al., "A Simple and Low-cost Method of Sleeve to Insert Silicone Gel Breast Implants," Plastic and Reconstructive Surgery Global Open, Sep. 2019, 7(9), 4 pages.

PCT International Search Report and Written Opinion in International Appln. No. PCT/US2021/058312, dated Feb. 24, 2022, 14 pages.

Shiao, "Implant Injector and Plastic Tube for Implantation of Silicone Textured Breast Prosthesis," The American Journal of Cosmetic Surgery, Sep. 1990, 7(3):181-3.

* cited by examiner

SURGICAL DELIVERY DEVICES, SYSTEMS, AND METHODS

CROSS-REFERENCE TO RELATED APPLICATION(S)

This is a continuation of U.S. patent application Ser. No. 17/519,039 filed on Nov. 4, 2021 and entitled "SURGICAL DELIVERY DEVISES, SYSTEMS, AND METHODS," which is a continuation of U.S. patent application Ser. No. 17/518,090 filed on Nov. 3, 2021 and entitled "SURGICAL DELIVERY DEVICES, SYSTEMS, AND METHODS," which is a continuation of U.S. patent application Ser. No. 17/092,017 filed on Nov. 6, 2020 and entitled "SURGICAL DELIVERY DEVICES, SYSTEMS, AND METHODS," the entire contents of which are incorporated herein by reference.

TECHNICAL FIELD

This document describes surgical delivery devices, systems, and methods, for example, surgical delivery devices that facilitate delivery of an implant to a surgical location.

BACKGROUND

Implants have been surgically delivered to provide heath and/or cosmetic benefits to the recipient, such as prosthetic devices, organs, tissues, etc. The implants may be carefully delivered by a healthcare practitioner to achieve a desired positioning within a surgical pocket.

SUMMARY

Some embodiments described herein include surgical delivery devices, systems, and methods that facilitate delivery of an implant into a patient, such as a silicone implant configured to reside under a person's skin. For example, a surgical delivery device can provide a flexible sleeve or guide into which an implant can be loaded and subsequently dispensed toward a targeted site, such as optionally a surgical opening of a patient. The surgical delivery device can optionally facilitate sterile handling of the implant, and delivery through a relatively small surgical opening (e.g., compared to the size of the implant, the surgical pocket under the skin, or both). In an example embodiment, the surgical delivery device is customizable at a time of use in the operating environment to achieve any of a variety of shapes that suit a particular application, patient anatomy, delivery location on the patient, surgical opening size, implant size/type, and/or healthcare practitioner ergonomics and operating preferences.

Some surgical delivery devices disclosed herein can be selectively shaped as desired by a practitioner to provide, for example, a tubular sleeve, a tapered guide conduit (e.g., which may provide a tapered region between a wider first end and a narrower second end), a pair of tapered guide conduits, or other selected shapes. The surgical delivery device optionally includes one or more handles, which can be suitable for a user to open or manipulate the delivery device without directly contacting an interior wall of the device. The handles can be attached on an exterior of the device, (e.g., an exterior of a polymer sheet that forms the sleeve or tapered guide conduit), and can facilitate manipulation of the surgical delivery device without contacting an interior surface or lateral edges of the device. For example, the handles can provide a grasping location when expanding the surgical delivery device into a sleeve, tapered guide conduit, or other selected shape, such as by pulling opposite sides of the device away from one another. In some embodiments, the user may elect to contact edges or interior of the device with a properly sterilized glove, instrument, etc., as an alternative or in addition to grasping the handles.

In some embodiments, the surgical delivery device is optionally constructed of first and second polymer sheets that are joined around a perimeter to define a sealed cavity. At a time of use, the surgical delivery device can be cut to unseal the cavity and/or provide one or more openings sized to receive and/or dispense an implant.

Some example surgical delivery devices are configured to be separable into two or more delivery sleeves or tapered guide conduits. A single surgical delivery device can thus provide two portions that can be used independently to deliver first and second implants, such as a pair of breast, gluteal, or calf implants. The single surgical delivery device is separated by cutting (e.g., using a surgical scissors, Mayo scissors, surgical blade, or other sterilized cutting instrument), tearing, or otherwise dividing the surgical delivery device into two or more portions. The surgical delivery device optionally defines a sealed cavity when packaged and does not include an opening to an interior of the surgical delivery device (e.g., to an interior of polymer sheets that define the cavity). The sealed cavity can be unsealed when cut at the time of use in the operating environment.

Particular embodiments described herein provide a method of using a surgical delivery device, including cutting a surgical delivery device into first and second portions, cutting a sealed end region of the first portion to provide a delivery opening, expanding the first portion of the delivery device, loading an implant within the cavity of the first portion, and dispensing the implant into the surgical opening through the end opening of the first portion.

In some implementations, the system can optionally include one or more of the following features. The method can include unfolding the surgical delivery device before cutting the surgical delivery device into first and second portions. The surgical delivery device can be in a planar configuration when cutting the surgical delivery device into first and second portions. Before cutting the surgical delivery device, the surgical delivery device can define a sealed cavity. The sealed cavity can be defined between two planar flexible polymer sheets. The sealed cavity can contain a lubricant. The method can include kneading the surgical delivery device to spread the lubricant along the interior surface of the cavity. The cavity can include a cylindrical section and a tapered section. The end opening of the first portion can have a size corresponding to a surgical opening of a patient. The end opening of the first portion can have a size corresponding to a size of the implant to be delivered to the patient. Expanding the first portion can include grasping handles located on the exterior of the first portion. Cutting the sealed end region of the first portion can include using a sizing tool to select a location to cut the sealed end region. The method can include cutting an end region of the second portion to provide an end opening having a size corresponding to a surgical opening of a patient, expanding the second portion of the delivery device, positioning a second implant within a cavity of the second portion, and dispensing the second implant into the surgical opening through the end opening of the second portion.

Particular embodiments described herein provide a device for delivering an implant into a surgical opening of a patient. The device includes a polymer body having first and second tapered sections and a sealed cavity defined by the polymer body. The polymer body is separable between the first and second tapered sections.

In some implementations, the system can optionally include one or more of the following features. The polymer body can include a rectangular section between the first and second tapered sections. The polymer body can include first and second planar sheets, the first planar sheet sealed to the second planar sheet around a perimeter of the first planar sheet. The polymer body can be entirely opaque. The device can include a series of indicia on the polymer body located at ends of each of the first and second tapered sections. The device can include one or more markings indicative of a predetermined cut locations. The one or more markings can be indicative of predetermined cut locations that include a first marking at a midline of the polymer body, a second marking between the rectangular section and the first tapered section, and a third marking between the rectangular section and the second tapered section.

The devices, system, and techniques described herein may provide one or more of the following advantages. First, some embodiments described herein include a surgical delivery device that is separable into two or more sleeves or tapered guide conduits. A single surgical delivery device can be separable at a time of use to provide multiple sleeves or tapered guide conduits. Such a configuration may promote sterility and efficiency in the operating environment, and/or facilitate delivery of a pair or group of implants, such as a pair of breast, gluteal, or calf implants, etc.

Second, some embodiments described herein include a sealed/sterile cavity when packaged. For example, the surgical delivery device can be unsealed (e.g., by cutting the surgical delivery device into two or more portions) at the time of use in the operating environment. Such a configuration can promote sterility of the interior of the surgical delivery device, and promote efficiency by streamlining sterilization procedures before introducing the surgical delivery device into a sterile surgical field.

Third, a size of the delivery opening can be selected to impart a desired level of compression or conformance on the implant as it is delivered through the delivery opening. For example, the surgical delivery device can be customized at a time of use to have a relatively small opening for delivery of implants (e.g., breast, gluteal, or calf implants, etc.) that are readily conformable, and/or that may be compressed during delivery to facilitate positioning of the implant within the surgical pocket of the patient. The surgical delivery device can be customized at a time of use to have a relatively larger opening for delivery of implants (e.g., tissues, organs, etc.) without compression or conformance of the implant as it is dispensed.

Fourth, a degree of taper or relative difference in size between openings at opposite ends may be customized. For example, an example surgical delivery device can be customizable to have no taper between first and second opposite end openings, such that the first and second openings have a same size. In some embodiments, the surgical delivery device can be customizable to have a substantial taper between first and second ends. Such customizability provides flexibility to a healthcare practitioner in selecting a surgical delivery device configuration that promotes effective and efficient delivery of an implant. The surgical delivery device configuration can be selected, for example, based on one or more of the application, patient anatomy, delivery location on the patient, surgical opening size, implant size, implant type, and/or healthcare practitioner ergonomics and operating preferences.

Fifth, some surgical delivery devices described herein facilitate handling and manipulation by the healthcare practitioner. For example, handles on an outside of the surgical delivery device facilitate manipulation without direct contact with inner surfaces or lateral edges of the device, promoting sterility during use. The handles may provide a grasping location as an alternative or in addition to the practitioner contacting edges or an interior of the device with a properly sterilized glove, instrument, etc. Alternatively or additionally, handles can provide secure grasping locations that facilitate handling by the healthcare practitioner while loading the implant and or delivery of the implant through the surgical delivery device.

Sixth, some embodiments described herein facilitate delivery of a relatively large implant through a relatively small surgical opening. A size of a delivery opening of the surgical delivery device may be selected based on the size of the implant and/or surgical opening. The implant can be compressed, elastically deformed, or otherwise conformed to fit through the surgical opening as the implant is dispensed through the delivery opening. Some example surgical devices described herein can thus facilitate use of a small surgical opening, reducing patient trauma and improving patient outcomes.

Seventh, some surgical delivery devices described herein facilitate efficient manufacturing that provides a robust construction that can be manufactured efficiently in large quantities. For example, in some optional embodiments, planar sheets of flexible polymer material can be efficiently cut and attached to one another to form the surgical delivery device, such as by heat welding first and second planar sheets to form a body of the surgical delivery device, and attaching additional planar polymer sheets (e.g., to an exterior of one or both of the first and second planar sheets) to form one or more handles.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1:
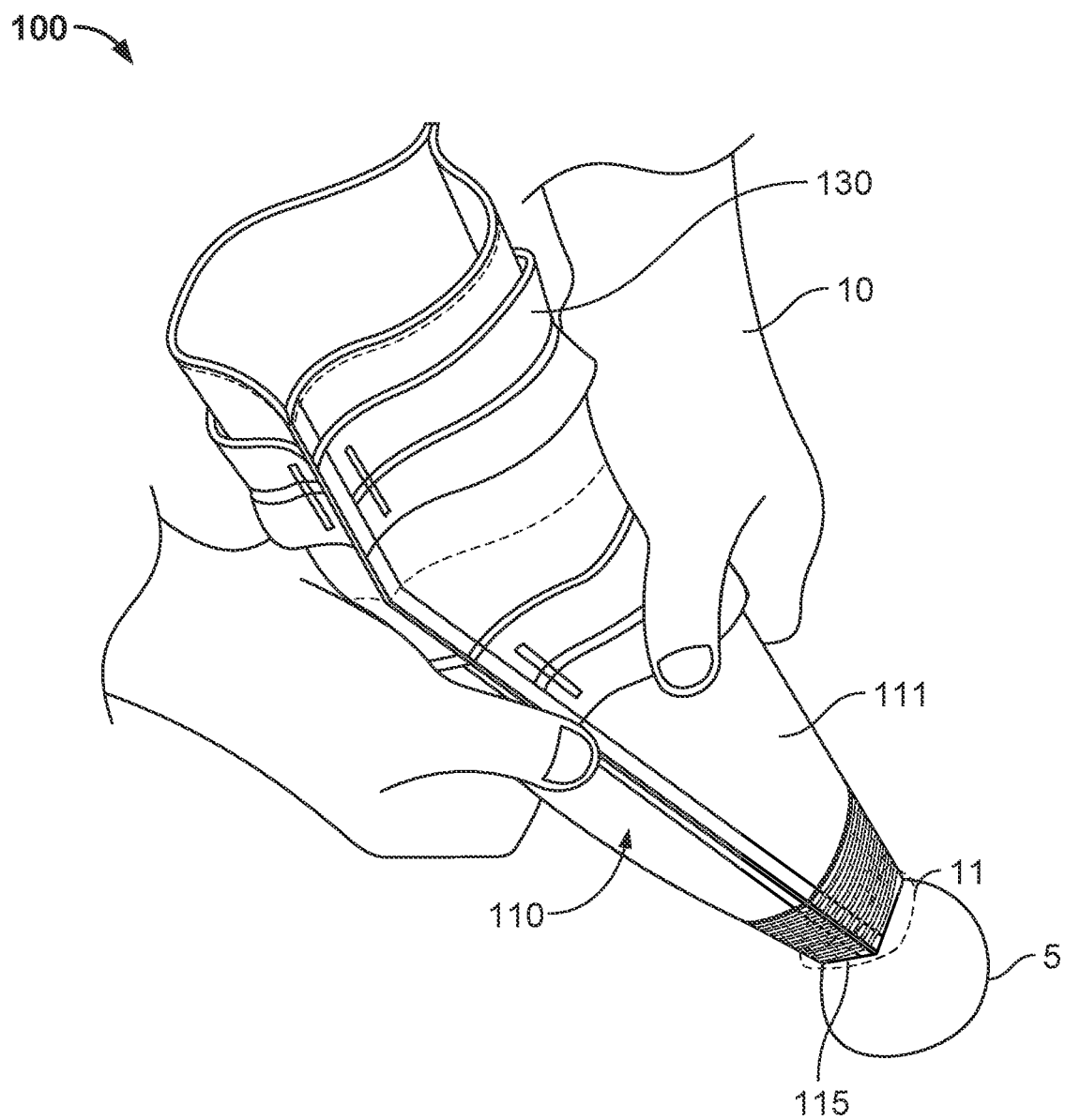
FIG. 1 is a perspective view of an example surgical delivery device in use.

Referring to FIG. 1, an example surgical delivery device 100 is shown. Surgical delivery device 100 facilitates delivery of an implant 5 into a surgical opening 11 of a patient. For example, surgical delivery device 100 can be optionally shaped to provide at least one tapered guide conduit 110 that defines an internal cavity to receive implant 5, and a delivery opening 115 to dispense the implant into a targeted surgical opening 11. Surgical delivery device 100 may facilitate efficient handling and delivery of an implant into a patient, while reducing the likelihood or frequency of a user directly contacting the implant 5 and/or an interior of surgical delivery device 100.

Surgical delivery device 100 includes one or more features that facilitate handling and manipulation of surgical delivery device 100. In an example embodiment, surgical delivery device 100 includes one or more handles 130 on an exterior of surgical delivery device 100 that provide grasping locations for a user 10. For example, handles 130 can facilitate opening surgical delivery device 100 (e.g., by pulling opposite sides of surgical delivery device 100 away from one another). Alternatively or additionally, handles 130 can facilitate a secure grip when force is exerted on surgical delivery device 100, such as when an implant is loaded into surgical delivery device 100. After an implant has been loaded into the surgical delivery device 100, implant 5 may be manipulated (e.g., via flexible walls 111 and/or handles 130) to dispense implant 5 through delivery opening 115 and into surgical opening 11.

Surgical delivery device 100 facilitates delivery of implant 5 through surgical opening 11 and into a patient. For example, delivery opening 115 can be about the same size or slightly smaller than surgical opening 11, and/or smaller than implant 5. A relatively small delivery opening 115 can facilitate delivery of a relatively larger implant 5 into surgical opening 11. The walls 111 of surgical delivery device 100 can facilitate compression of implant 5 as implant 5 moves toward and through delivery opening 115, reducing a dimension of implant 5 in at least one direction. Surgical delivery device 100 can thus facilitate delivery of a relatively large implant 5 through a relatively small surgical opening 11, reducing patient trauma and facilitating positive patient outcomes.

In various example embodiments, surgical delivery device 100 is compatible with various types of implants and surgical applications. For example, surgical delivery device 100 can facilitate handling and delivery of a prosthetic implant 5, such as a breast, gluteal, calf, pectoral, and/or facial implant. Optionally, prosthetic implant 5 is a silicone implant structure that is flexible and configured to reside in a targeted surgical pocket under a patient's skin. Prosthetic implant 5 can be loaded into the surgical delivery device (e.g., directly from the sterile packaging of the implant 5), and then compressed, conformed, or otherwise manipulated via the surgical delivery device 100 as it is dispensed into a surgical opening. Alternatively or additionally, surgical deliver device 100 facilitates handling and delivery of a tissue implant 5, such as an organ, tissue, or other cellular implant. As described in detail below, the user can select/customize the size and shape of the surgical delivery device 100, load the implant 5 (prosthetic or tissue) into the surgical delivery device 100, and then direct the implant 5 through the surgical delivery device 100 (for dispensation through the delivery opening 115) and into the surgical opening—all of which can be optionally achieved without directly contacting the implant 5 with the user's (gloved) hands. Alternatively, the user may elect to manually adjust or otherwise directly manipulate the implant 5 with the user's (gloved) hands during loading or during transfer through the delivery device 100 so as to facilitate a preferred orientation or position of the implant within the delivery device 100.

Figure 2:
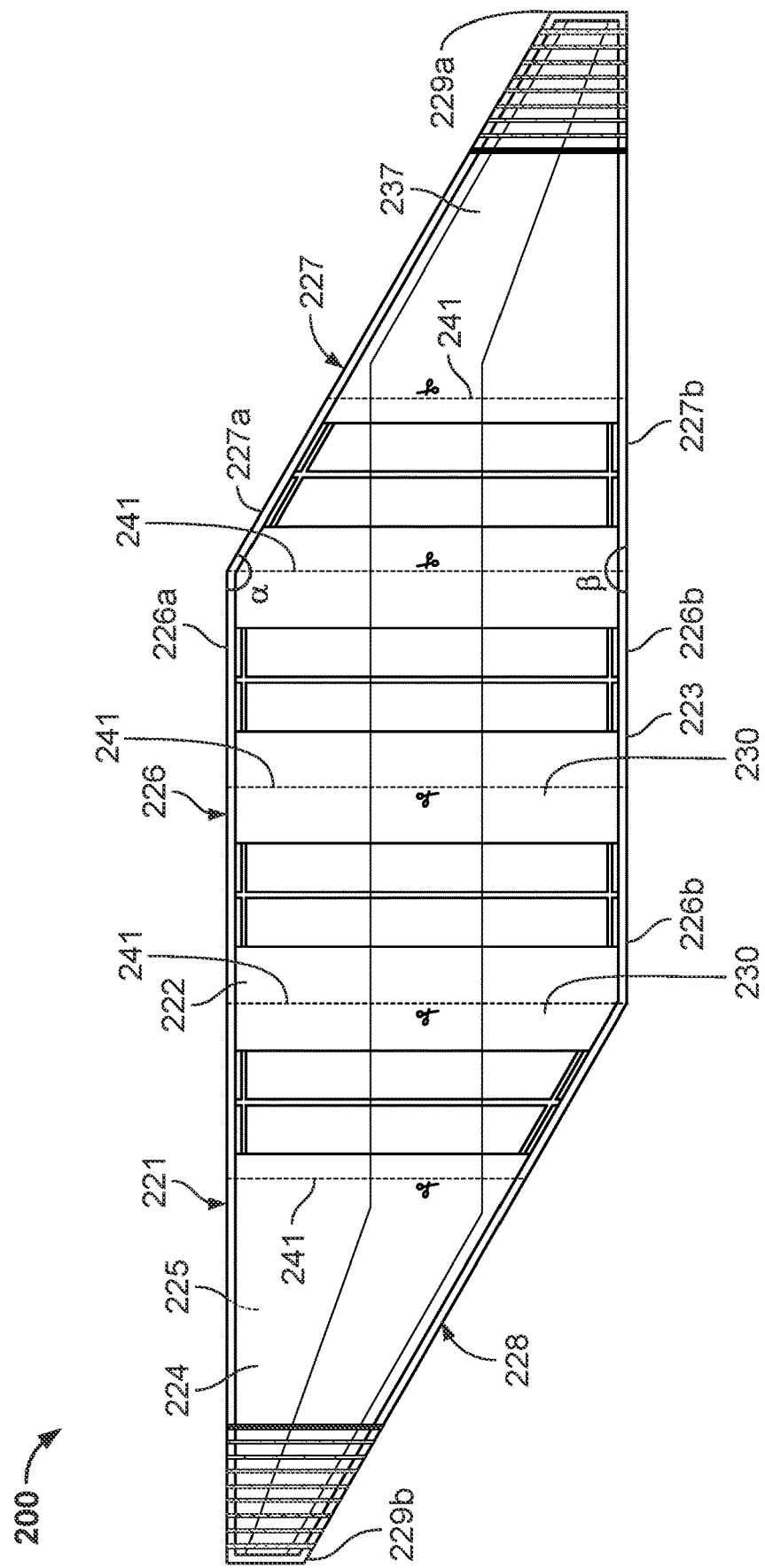
FIG. 2 is a plan view of an example surgical delivery device.

Referring now to FIG. 2, a plan view of an example surgical delivery device 200 is shown. In various example embodiments, surgical delivery device 200 includes one or more features as described herein with reference to surgical delivery device 100.

Surgical delivery device 200 facilitates efficient and effective delivery of an implant through a surgical opening of a patient. Surgical delivery device 200 is customizable at a point of use, such as in a surgical theater or other operating environment, to provide one or more customized delivery sleeves, tapered guide conduits, or other guide structures having a selected geometry for the user's particular application. For example, surgical delivery device 200 can be customized to provide a selected taper and/or one or more openings having a selected size based on the application, patient anatomy, delivery location on the patient, surgical opening size, implant size, implant type, and/or healthcare practitioner ergonomics and operating preferences.

Surgical delivery device 200 includes a polymer body 221 that defines an internal cavity 222. Polymer body 221 may be made from one or more flexible polymer materials. For example, polymer body 221 includes one or more flexible polymer layers that define cavity 222. In an example embodiment, polymer body 221 includes first and second flexible polymer sheets 224, 225. First flexible polymer sheet 224 is attached to second flexible polymer sheet 225 to define cavity 222 between first and second flexible polymer sheets 224, 225. In an example embodiment, polymer body 221 includes one or more seams 223 where first flexible polymer sheet 224 is attached to second flexible polymer sheet 225. The first and second flexible polymer sheets 224, 225 can be joined by heat staking to form seam 223. Alternatively or additionally, first and second flexible polymer sheets 224, 225 can be joined by welding, adhesive, rivets, etc.

In some embodiments, polymer body 221 is formed by a single flexible polymer layer or sheet 224. The single flexible polymer layer or sheet 224 is folded and attached to itself to define cavity 222. Alternatively or additionally, the single polymer layer or sheet 224 is provided by an extruded or formed polymer layer that does not include a visible seam, includes only one or more seams at opposite narrow ends, or is otherwise formed without a visible seam (e.g., without a seam along the length of polymer body 221).

In an example embodiment, cavity 222 is entirely sealed such that surgical delivery device 200 does not include an opening into cavity 222 (e.g., when packaged). Such a configuration can promote sterility of cavity 222, reducing or streamlining sterilization procedures in the operating environment at the time of use. In some embodiments, a lubricant (e.g., a wet lubricant, dry lubricant, non-film lubricant), antimicrobial/antibiotic material, and/or other component may be provided in cavity 222 (e.g., at a time of manufacture before entirely sealing cavity 222). An entirely sealed cavity can facilitate storage of such components without leaking, oxidation, or contamination. In some embodiments, one or both ends may be open such that cavity 222 is not entirely sealed.

In various example embodiments, the lubricant provided in cavity 222 can be a wet lubricant, such as a propylene glycol gel lubricant. The cavity 222 can be entirely sealed to contain the wet lubricant within cavity 222, and/or to prevent the wet lubricant from drying or otherwise degrading. In some embodiments, the lubricant can be a dry lubricant. The dry lubricant can be sprayed or otherwise delivered into cavity 222. The cavity 222 can be at least partially open or unsealed entirely sealed. For example, one or both ends of surgical delivery device 200 may remain unsealed when packaged for delivery at the time of manufacture. The dry lubricant may be lubricious in a dry condition and/or activated or enhanced when wetted. In an example embodiment, the dry lubricant provides lubrication without forming a film (e.g., the dry lubricant does not create a film when wetted and functioning as a lubricant).

Surgical delivery device 200 has a shape that facilitates separation into one or more tubular sleeves or tapered guide conduits (e.g., non-symmetrical tapered guide conduits), and/or delivery of an implant through the one or more sleeves or tapered guide conduits. In an example embodiment, when in a flattened configuration, surgical delivery device 200 includes a generally trapezoidal shape having a rectangular section 226, and one or more tapered sections 227, 228. For example, rectangular section 226 may be a middle section located between tapered sections 227, 228. In an example embodiment, rectangular section 226 has a consistent diameter along its length, and is manipulable into an expanded configuration to define a cylindrical sleeve portion. Tapered sections 227, 228 have a triangular shape that tapers between rectangular section 226 and ends 229a, 229b, and are manipulable into an expanded configuration to define tapered guide portions.

In an example embodiment, an edge 227a of tapered section 227 defines an angle α relative to an edge 226a of rectangular section 226. A larger angle α can provide a relatively shallower taper and/or a relatively longer tapered section 227, and a smaller angle α can provide a relatively steeper transition and/or a shorter tapered section 227. In various example embodiments, angle α is between 110° and 170°, 130° and 160°, or about 150°. Alternatively or additionally, an edge 227b of tapered section 227 defines an angle β relative to an edge 226b of rectangular section 226. In an example embodiment, edges 227b and 226b are colinear, such that angle β is 180°. In such embodiments, the tapered section 227 includes a tapered edge 227a that is opposite from a non-tapered edge 227b. The device can be expanded to define a non-symmetrical tapered delivery conduit. In alternative example embodiments, angle β is between 110° and 170°, 130° and 160°, or about 150°.

Tapered section 228 has similar proportions to tapered section 227. For example, tapered section 228 has the same proportions and angles as tapered section 227. Cutting the surgical delivery device in half yields two surgical delivery device portions having the same geometry. In an example embodiment, the tapered section 228 has the same geometry as tapered section 227 and is not arranged as a mirror image of tapered section 227. Such a configuration can facilitate efficient manufacturing by allowing multiple polymer body portions to be cut while reducing waste material.

In some embodiments, tapered section 228 has one or more different dimensions compared to tapered section 227. Tapered sections 228, 227 having different dimensions can provide a sleeve or tapered guide conduit having different geometry, and/or facilitate customizability by the user.

Surgical delivery device 200 includes one or more handles 230. Handles 230 facilitate manipulation of the surgical delivery device. In an example embodiment, surgical delivery device 200 includes multiple handles 230 at different locations. Surgical delivery device 200 can be cut into two or more portions while each of those portions include one or more handles 230. Alternatively or additionally, multiple handles 230 are provided on opposite sides of surgical delivery device 200. Handles 230 positioned on opposite sides of surgical delivery device 200 can facilitate adjustment of surgical delivery device 200 into an expanded configuration (e.g., after making a cut through surgical delivery device 200). In an example embodiment, rectangular section 226 includes two sets of handles 230 on opposite sides of surgical delivery device 200, and each of tapered sections 227, 228, include one set of handles 230 on opposite sides of surgical delivery device 200.

Handles 230 are attached to an exterior of surgical delivery device 200. In an example embodiment, handles 230 include strips of polymer material attached with polymer body 221. Handles 230 are welded or otherwise secured with body 221 to form a flap or tab that can be grasped by the user. Handles 230 lay flat against a portion of body 221 when surgical delivery device 200 is in a planar configuration, and at least partially extend outwards from body 221 when grasped by a user. In some example embodiments, handle 230 are integrally formed as a portion of body 221 (e.g., a portion of flexible polymer layers 224 and/or 225).

In an example embodiment, surgical delivery device 200 is opaque. For example, the flexible polymer material of body 221 is a white polymer such that body 221 is not transparent. An implant or other material within cavity 222 is not readily visible through the body 221. Alternatively, some or all of body 221 can be substantially transparent such that an implant or other material within cavity 222 is at least partially visible. For example, body 221 can include one or more transparent windows, such as a strip of transparent material 237 that extends partially or completely between ends 229a, 229b. In an example embodiment, body 221 is not mostly or entirely transparent.

Surgical delivery device 200 includes indicia that facilitates customization and/or use. For example, surgical delivery device 200 includes markings 241 that designate predetermined cut locations. Surgical delivery device 200 includes a cut location marking 241 across a midline of surgical delivery device 200, at an interface between rectangular section 226 and tapered sections 227, 228, respectively, and at one or more locations of surgical device 200, such as across tapered sections 227, 228. The user can cut or otherwise separate surgical delivery device 200 at these locations to form two or more surgical delivery device portions having predetermined geometries. In an example embodiment, markings 241 include printed indicia. Alternatively or additionally, markings 241 include a weakened line or other physical feature that facilitates cutting or separation of surgical delivery device 200.

Surgical delivery device 200 includes a series of markings 242 proximate ends 229a, 229b that facilitate creation of a delivery opening having a predetermined size or geometry. In an example embodiment, markings 242 include a series of lines that differ in visual appearance and correspond to different delivery opening sizes. For example, the markings can correspond to a width, circumference, diameter, etc., at the location of the respective marking on surgical delivery device 200, such as a width, circumference, diameter of 4.0 cm, 4.5 cm, 5.0 cm, 5.5 cm, 6.0 cm, 6.5 cm, 7.0 cm, 7.5 cm, 8.0 cm. Alternatively or additionally, the markings can correspond to a predetermined opening size to accommodate a particular implant size. For example, the markings can correspond to a predetermined opening size to accommodate an implant less than 315 cc, between 315 cc and 500 cc, 500 cc and 550 cc, 550 cc and 600 cc, 600 cc and 650 cc, 650 cc and 700 cc, or greater than 700 cc, for example. The user can cut along a selected line to create a delivery opening having a predetermined size suitable for a particular application. In various example embodiments, each of ends 229a, 229b include between 3 and 20, 5 and 15, or 6 and 10 markings 242.

Figure 3:
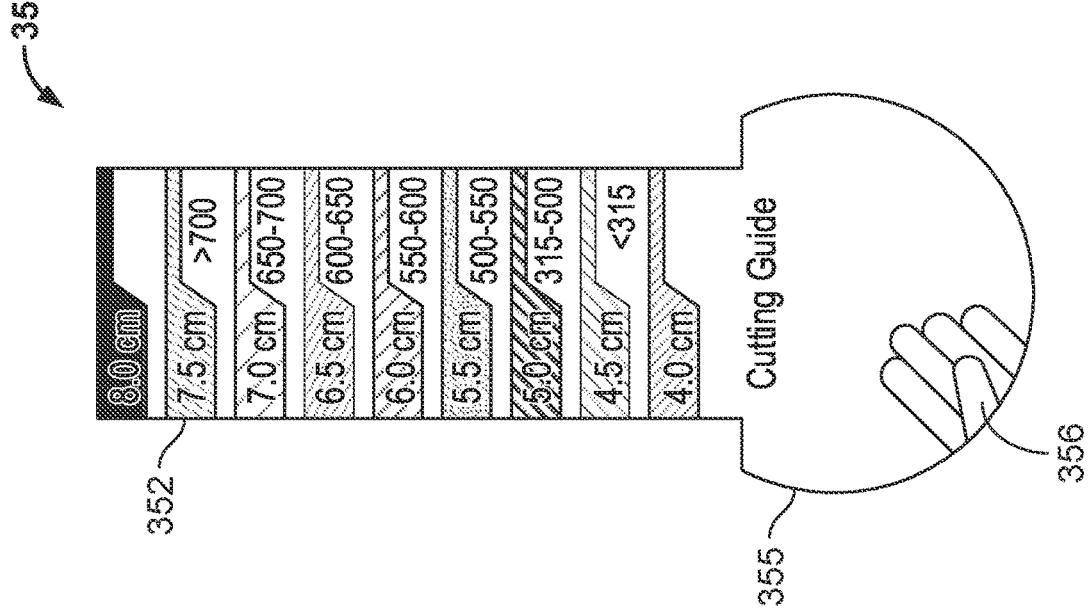
FIG. 3 is a sizing tool for use with the example surgical delivery device of FIG. 2.

Referring now to FIG. 3, an example sizing tool 350 is shown. The sizing tool can be used to select an appropriate delivery opening size. For example, sizing tool 350 includes one or more markings 352 corresponding to one or more of markings 242 (FIG. 2) proximate ends 229*a*, 229*b* of surgical delivery device 200. Markings 352 include delivery opening sizes and/or implant characteristics (e.g., volume) associated with particular markings 242.

During use, the user can locate the marking 352 that lists a desired delivery opening size and/or implant characteristic. The user can then locate the corresponding marking 242 based on the matching visual appearance (e.g., color, line type, etc.) on surgical delivery device 200. Surgical delivery device 200 can be cut along the identified line to create a delivery opening having the selected size.

In some embodiments, sizing tool 350 can be used to create delivery openings having predetermined sizes instead of markings on surgical deliver device 200 (e.g., instead of markings 242). For example, a user can align sizing tool 350 with an end 229*a*, 229*b* of surgical deliver device 200 to determine where to cut the surgical delivery device. Sizing tool 350 thus serves as a measuring tool that can be used to measure and/or identify a cut location at ends 229*a*, 229*b*.

Sizing tool 350 includes a handle or grasping portion 355. The grasping portion can include an enlarged area to facilitate handling. Alternatively or additionally, sizing tool 350 includes indicia of a hand 356 that provides a visual instruction that the sizing tool 350 can be handled using grasping portion 355, and/or indicia or physical features that facilitate alignment with ends 229*a*, 229*b*, when identifying a cut location on surgical delivery device 200.

Figure 4:
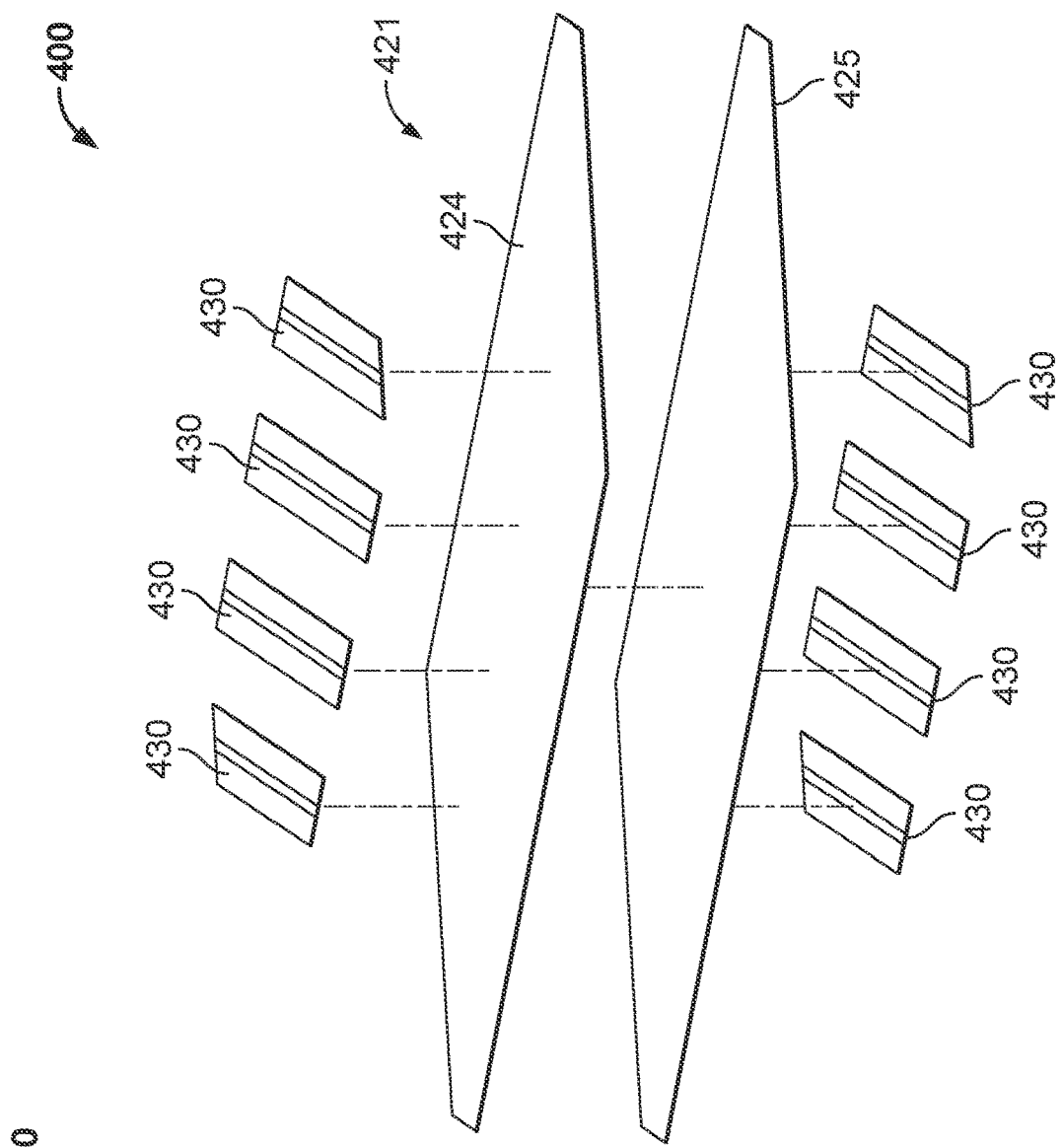
FIG. 4 is an exploded view of an example surgical delivery device.

Referring now to FIG. 4, a partial exploded view of an example surgical delivery device 400 is shown. In various example embodiments, surgical delivery device 400 includes one or more features as described herein with reference to surgical delivery devices 100 and 200.

Surgical delivery device 400 includes a polymer body 421 that includes first and second polymer sheets 424, 425. First and second polymer sheets 424, 425 are formed from a polyvinylchloride (PVC) material, such as a medical grade PVC. In various example embodiments, the material has a thickness between 2 mm and 30 mm, 4 mm and 15 mm, 6 mm and 12 mm, or a thickness of about 8 mm. Alternatively or additionally, first and second polymer sheets 424, 425 are formed from a polypropylene, polyethylene, polyethylene terephthalate, polystyrene, polyamide, polyurethane, and/or silicone.

The first and second polymer sheets 424, 425 can be cut into from bulk sheet stock, such as by die cutting. The trapezoidal shape of first and second polymer sheets 424, 425 can facilitate efficient manufacturing of first and second polymer sheets 424, 425 from bulk sheet stock while reducing the amount of waste material that results from a cutting operation.

First and second polymer sheets 424, 425 are attached to one another in a sealing operation. For example, first and second polymer sheets 424, 425 can be sealed to one another at least partially around perimeter edges of first and second polymer sheets 424, 425. After first and second polymer sheets 424, 425 are attached to one another, a cavity is formed between first and second polymer sheets 424, 425. The first and second flexible polymer sheets 424, 425 can be joined by heat staking, and/or welding, adhesive, rivets, or other techniques.

In an example manufacturing operation, first and second polymer sheets 424, 425 are attached along a portion of respective perimeters such the entire perimeters are not attached. An additive, such as a fluid lubricant, antimicrobial/antibiotic material, and/or other component, can be introduced into the cavity formed between first and second polymer sheets 424, 425. The first and second polymer sheets 424, 425 can be attached along the remaining portions of respective perimeter edges to seal the additive between the first and second polymer sheets 424, 425. Such a manufacturing technique can facilitate introduction of an additive between first and second polymer sheets 424, 425, and provide a cavity between first and second polymer sheets 424, 425 that is entirely sealed. In some embodiments, interior surfaces of first and second polymer sheets 424, 425 are sterilized and/or assembled in a sterile environment, promoting sterility of the cavity formed between first and second polymer sheets 424, 425 and reducing or streamlining sterilization procedures in the operating environment at the time of use.

Surgical delivery device 400 includes one or more handles 430 attached to exterior surfaces of first and second polymer sheets 424, 425. Handles 430 are formed from a polyvinylchloride (PVC) material, such as a medical grade PVC. In various example embodiments, the material has a thickness between 2 mm and 30 mm, 4 mm and 15 mm, 6 mm and 12 mm, or a thickness of about 8 mm. Alternatively or additionally, handles 430 are formed from a polypropylene, polyethylene, polyethylene terephthalate, polystyrene, polyamide, polyurethane, and/or silicone. In an example embodiment, handles 430 are formed from the same material as first and/or second polymer sheets 424, 425 (e.g., same material composition, thickness, color, opacity, texture, etc.). In some embodiments, handles 430 is formed from a material that differs from the material of first and/or second polymer sheets 424, 425 in one or more characteristics, such as material composition, thickness, color, opacity, texture, etc.

The handles 430 can be cut into from bulk sheet stock, such as by die cutting. The handles are attached to first and second polymer sheets 424, 425, respectively, such as by heat staking, and/or welding, adhesive, rivets, or other techniques.

Referring now to FIGS. 5A-5G, an example use of a surgical delivery device 500 is shown. In various example embodiments, surgical delivery device 500 includes one or more features as described herein with reference to surgical delivery devices 100, 200, 400, and surgical delivery devices 100, 200, 400 are configured for use including one or more operations described with reference to surgical delivery device 500.

Figure 5A:
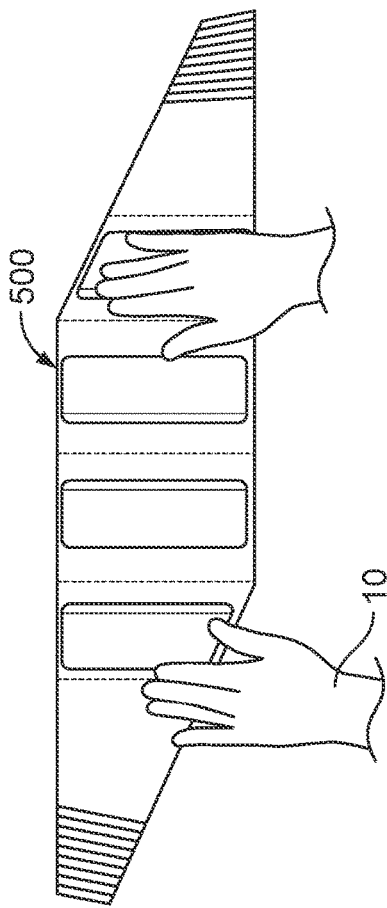
FIGS. 5A-5G show use of an example surgical delivery device.

Referring to FIG. 5A, an example opening operation of surgical delivery device 500 is shown. The example opening operation includes removing surgical delivery device 500 from packaging. In some embodiments, surgical delivery device 500 is packaged in a protective wrapper at a time of manufacture, such as a protective wrapper to promote sterility and/or mechanical integrity, reduce UV exposure, etc. The user 10 can remove surgical delivery 500 from the protective rapper in the operating environment at a time of use. In some embodiments, surgical delivery device 500 is packaged in a folded configuration in which the surgical delivery device 500 is folded over itself at one or more locations (e.g., to fit in a predetermined package size). The example opening operation can include unfolding, unrolling, or otherwise opening surgical delivery device 500 into a planar configuration (e.g., such as a planar configuration shown in FIG. 2) and laying the surgical delivery device 500.

The example opening operation can be conducted using sterile techniques. For example, the packaging can be opened and passed into the sterile field, or handed to a user in the sterile filed using sterile techniques.

Figure 5B:
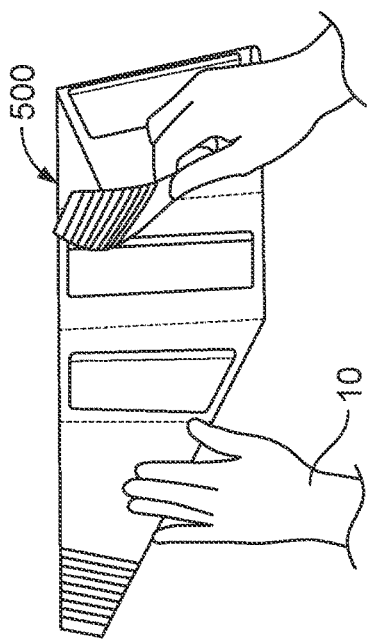

Referring to FIG. 5B, an example kneading operation of surgical delivery device 500 is shown. In the example kneading operation, user 10 can gently knead or otherwise manipulate the exterior of the tapered guide conduit to ensure an additive within surgical delivery device 500 is evenly spread throughout the cavity. For example, user 10 can press the surgical delivery device 500 to manipulate the additive to contact the entirety of internal surfaces that define the cavity of surgical delivery device 500. Alternatively or additionally, the example kneading operation includes smoothing the surgical delivery device 500 to adjust the surgical delivery device 500 into a planar configuration, remove creases, etc. In an example operating, kneading the surgical delivery device 500 occurs on a sterile surface (e.g., within a sterile field).

Figure 5D:
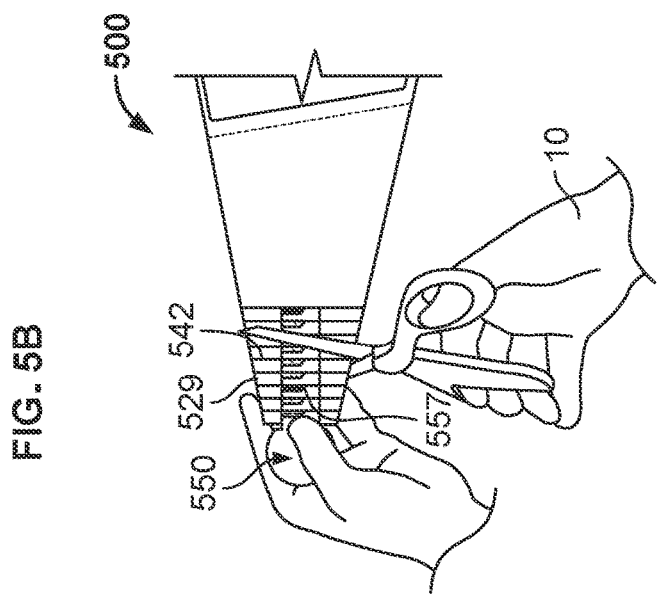
Figure 5C:
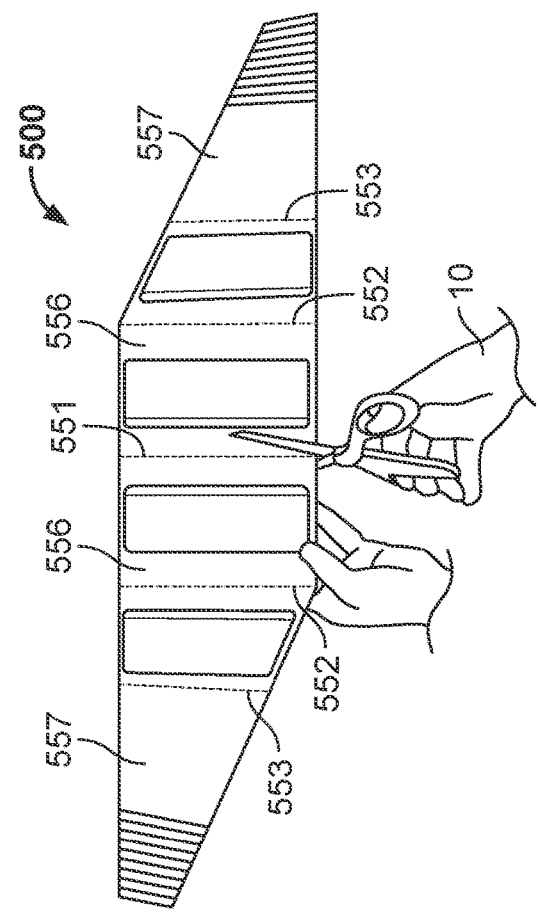

Referring to FIG. 5C, an example separating operation of surgical delivery device 500 is shown. Separating operation includes cutting, tearing (e.g., along a weakened material line), or otherwise dividing surgical delivery device 500 into two or more surgical delivery device portions. The user 10 can select a separation location based on a particular application, patient anatomy, delivery location on the patient, surgical opening size, implant size/type, and/or healthcare practitioner ergonomics and operating preferences. In an example embodiment, separating operation includes separating surgical delivery device 500 to form two surgical delivery device portions having similar geometry. For example, surgical delivery device 500 can be separated by cutting surgical delivery device 500 along a midline 551 of surgical delivery device 500 to provide two surgical delivery device portions. Each of the resulting surgical delivery device portions include a relatively larger, cylindrical region 556 and a tapered region 527.

In various example embodiments, the separating operation includes separating the surgical delivery device 500 at a location other than midline 551 of the surgical delivery device 500. Separating surgical delivery device 500 at a location other than midline 551 can result in a surgical delivery device portion having a selected configuration, or two or more surgical delivery device portions having different geometries. For example, the separating operation can include separating the surgical delivery device at a location where the surgical device begins to taper, such as line 552, a location along a tapered portion, such as line 553, or one or more other locations of surgical delivery device 500. In an example embodiment, the separating operating includes two or more cuts, such as at each of lines 552, to form a rectangular surgical delivery device portion that can be expanded into a cylindrical shape.

In an example embodiment, separating the surgical delivery device 500 includes unsealing the cavity of the surgical delivery device 500. For example, surgical delivery device 500 may be entirely sealed when removed from packaging at the time of use, such that there is no opening into the interior cavity. Separating the surgical delivery device 500 includes creating an opening into the cavity by cutting through the surgical delivery device 500. In an example embodiment, the separating operation includes simultaneously creating an opening in each of the first and second surgical delivery device portions that result from the separating operation.

Referring to FIG. 5D, an example trimming operation is shown. The trimming operation can be performed to provide a delivery opening having a selected geometry. In an example embodiment, surgical delivery device 500 includes a series of markings 542 proximate ends 529 that facilitates cutting surgical delivery device 500 to create a delivery opening having a selected size or geometry. For example, markings 542 include two or more lines having a different color, pattern, or other different visual appearance that correspond to different delivery opening sizes. In an example embodiment, markings 542 correspond to a width, circumference, diameter, etc., at the location of the respective marking. Alternatively or additionally, the markings can correspond to a delivery opening size configured to accommodate a particular implant size. In an example embodiment, trimming operation includes selecting a marking (e.g., based on the particular application, patient anatomy, delivery location on the patient, surgical opening size, implant size/type, and/or healthcare practitioner ergonomics and operating preferences), and cutting the surgical delivery device 500 along the line to form a delivery opening of predetermined geometry.

In an example embodiment, the trimming operation includes using a sizing tool 550 to select a cut location. Sizing tool 550 includes one or more markings 657 that correspond to markings 542 of surgical delivery device 500, and that are indicative of delivery opening sizes, implant dimensions (e.g., volume), or other characteristics that facilitate selecting a cut location. The trimming operating includes aligning sizing tool 550 with one or more of markings 542 proximate end 529 to select a cut location. After selecting a cut location, the trimming operating can include moving the sizing tool 550 away from end 529, and cutting the surgical delivery device 500 at the selected location.

In some embodiments, surgical delivery device 500 does not include a series of markings 542. The trimming operation includes aligning sizing tool 550 proximate end 529, and selecting a cut location using markings 557 (e.g., without reference to markings on the surgical delivery device 500).

Alternatively or additionally, sizing tool 550 can be used as a reference key. The trimming operation includes selecting a marking 542 on surgical delivery device 500 with reference to sizing tool 550 (e.g., without aligning sizing tool with end 529). For example, selecting a marking may include locating a marking 557 that corresponds with a desired delivery opening size and/or implant characteristic, and then locating the corresponding marking 542 on surgical delivery device 500 based on the matching visual appearance (e.g., color, line type, etc.).

Figure 5E:
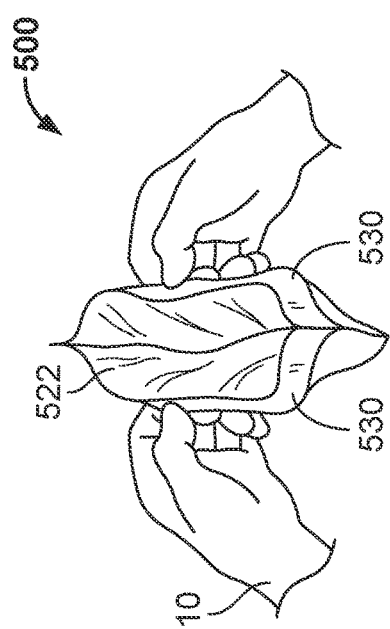

Referring now to FIG. 5E, an example opening operation is shown. Surgical delivery device 500 is manipulated from a first configuration (e.g., planar configuration) to a second configuration (e.g., expanded configuration). In an example embodiment, opening operation includes grasping handles 530 of surgical delivery device 500 and pulling opposites sides away from each other. Handles 530 facilitate opening of surgical delivery device 500, as an additional grasping location or as an alternative to direct contact with an interior of cavity 522 and/or lateral edges (e.g., that define an opening) of surgical delivery device 500.

Figure 5F:
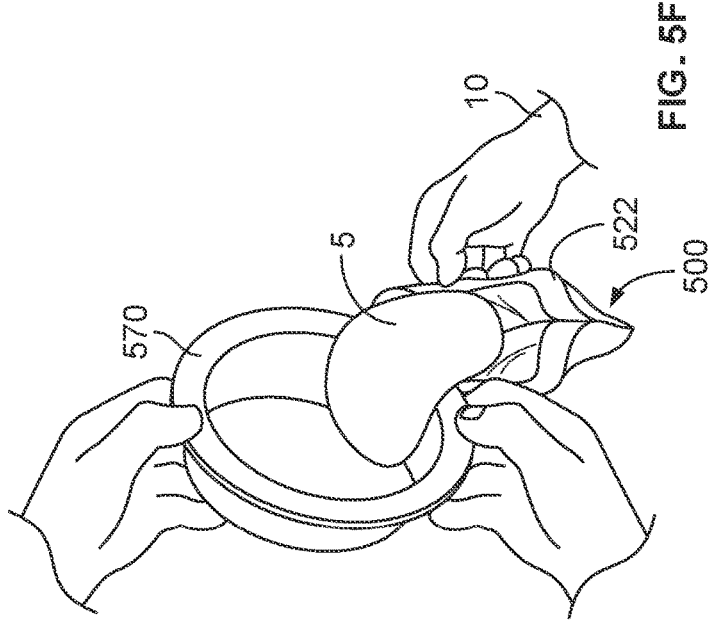

Referring to FIG. 5F, an example loading operation is shown. In an example embodiment, the loading operation includes pouring an implant 5 (e.g., from a sterile container 570) into the cavity 522 of surgical delivery device 500. A user may pour sterile solution into cavity 522 together with implant 5. In an example embodiment, a delivery opening is smaller than the size of implant 5 such that the implant can be retained in cavity 522 when surgical delivery device 500 is in a vertical orientation. Implant 5 may be a prosthetic implant, such as a silicone breast, gluteal, calf, pectoral, and/or facial implant. Alternatively or additionally, implant 5 may be a tissue implant, such as an organ, tissue, or other cellular implant.

Figure 5G:
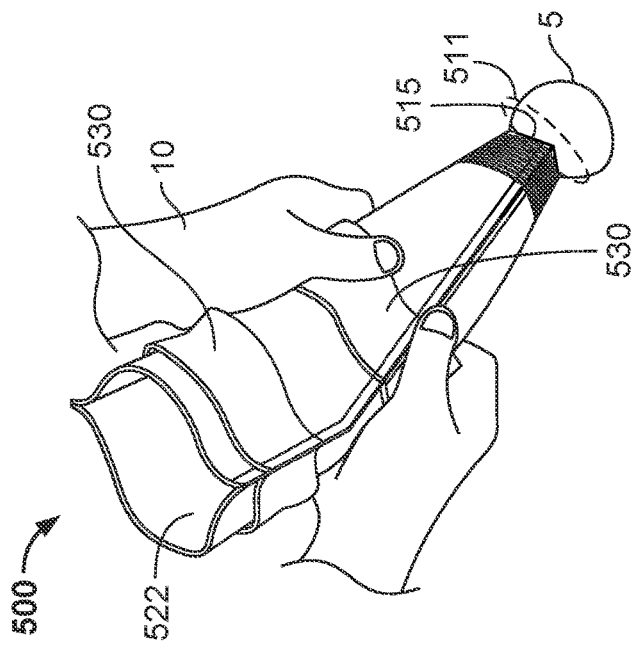

Referring to FIG. 5G, an example delivery operation is shown. In an example embodiment, the delivery operation includes dispensing implant 5 through the delivery opening 515 by squeezing or otherwise manipulating implant 5 using surgical delivery device 500. As user 10 pushes implant 5 through delivery opening 515, implant 5 can be compressed, elastically deformed, or otherwise conformed to fit through delivery opening 515 and into a surgical opening 511. In an example embodiment, compression of implant 5 as implant 5 passes through delivery opening 515 facilitates delivery into a relatively small surgical opening (e.g., compared to a size of implant 5), reducing patient trauma and improving patient outcomes.

User 10 can manipulate and/or push implant 5 through walls of surgical delivery device 500. In some embodiments, a user may grasp handles 530 with one or both hands during delivery to facilitate manipulation of implant 5 and/or advance implant 5 through delivery opening 515.

In an example embodiment, implant 5 can be delivered by surgical delivery device 500 without direct contact of implant 5 by the user. For example, the loading operation can be performed by pouring implant 5 directly into cavity 522, and the delivery operation can be performed by manipulating implant 5 through walls of surgical delivery device 500. In some embodiments, the user may elect to contact implant 5 during loading or delivery, such as by using a properly sterilized hand, glove, instrument, etc.

Figure 6:
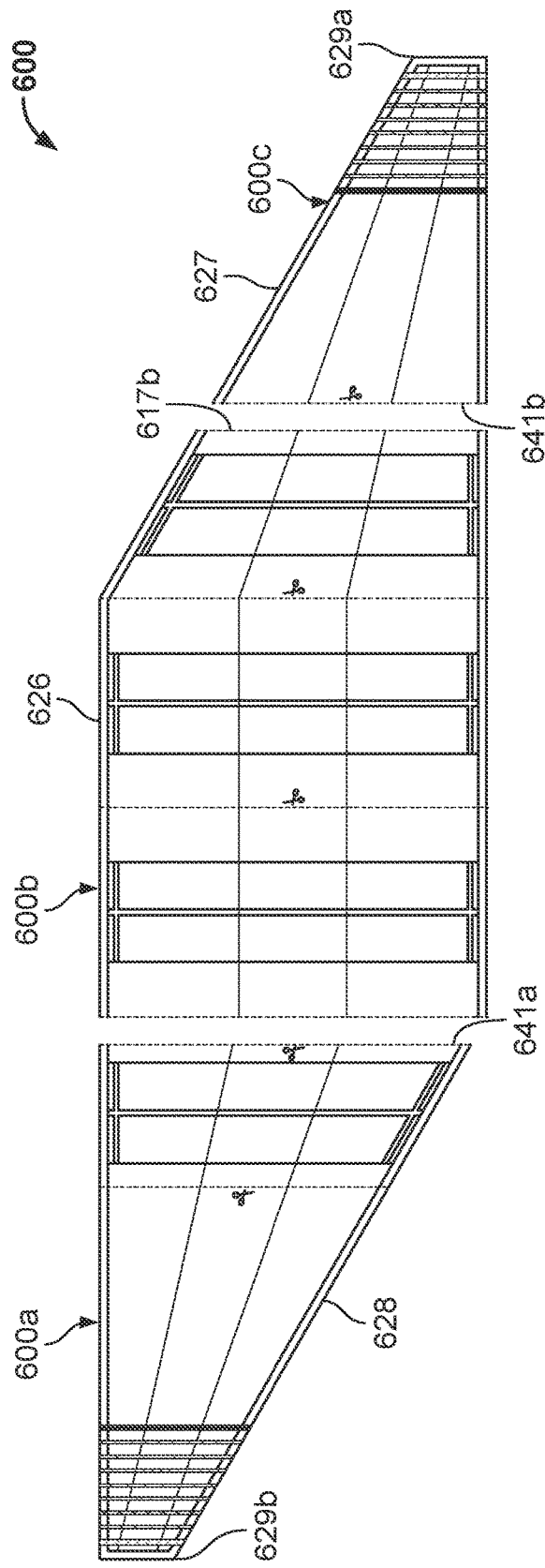
FIG. 6 shows an example surgical device separated into multiple portions.

Referring now to FIG. 6, a plan view of an example surgical delivery device 600 is shown separated into multiple portions. In various example embodiments, surgical delivery device 600 includes one or more features as described herein with reference to surgical delivery device 100, 200, 400, 500.

Surgical delivery device 600 is customizable at a point of use, such as in an operating environment, to provide one or more delivery sleeves or tapered guide conduits having a selected geometry for a particular application. Surgical delivery device 600 can be customized to provide a selected taper and/or one or more openings having a size based on the application, patient anatomy, delivery location to the patient, surgical opening size, implant size, implant type, and/or healthcare practitioner ergonomics and operating preferences. In an example embodiment, when in a flattened configuration, surgical delivery device 600 includes a generally trapezoidal shape having a rectangular section 626, and one or more tapered sections 627, 628. For example, rectangular section 626 may be a middle section located between tapered sections 627, 628. In an example embodiment, rectangular section 626 has a consistent diameter along its length, and is manipulable into an expanded configuration to define a cylindrical portion. Tapered sections 627, 628 have a triangular shape that tapers between rectangular section 626 and ends 629a, 629b, and are manipulable into an expanded configuration to define tapered guide portions.

Surgical delivery device 600 is shown separated into multiple surgical delivery device portions. For example, surgical delivery device 600 is shown separated into first, second, and third surgical delivery device portions 600a, 600b, 600c (e.g., formed by separating surgical delivery device 600 along markings 641a and 641b). In an example embodiment, marking 641a is located between rectangular section 626 and tapered section 628, and marking 641b is located on tapered section 627. As a result, surgical delivery device 600 is separated into portions 600a, 600b, 600c, having differing geometries and/or degrees of tapering. For example, portion 600b tapers to a relatively larger delivery opening 617b compared to portions 600a, 600c that taper to relatively smaller delivery openings (e.g., which can be formed by cutting surgical delivery device 600 proximate ends 629a, 629b).

A user can use each of portions 600a, 600b, and/or 600c to deliver implants to a single patient, such as to deliver multiple implants having differing sizes or characteristics to different surgical openings on the patient. In some embodiments, one or more portions 600a, 600b, 600c, may be discarded, and one or more portions 600a, 600b, 600c having selected geometry used to deliver an implant.

Figure 7A:
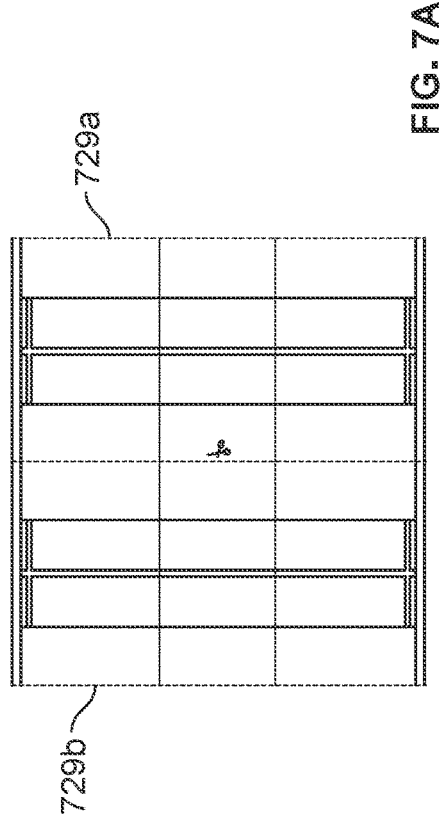
FIG. 7A shows an example surgical delivery device.
Figure 7B:
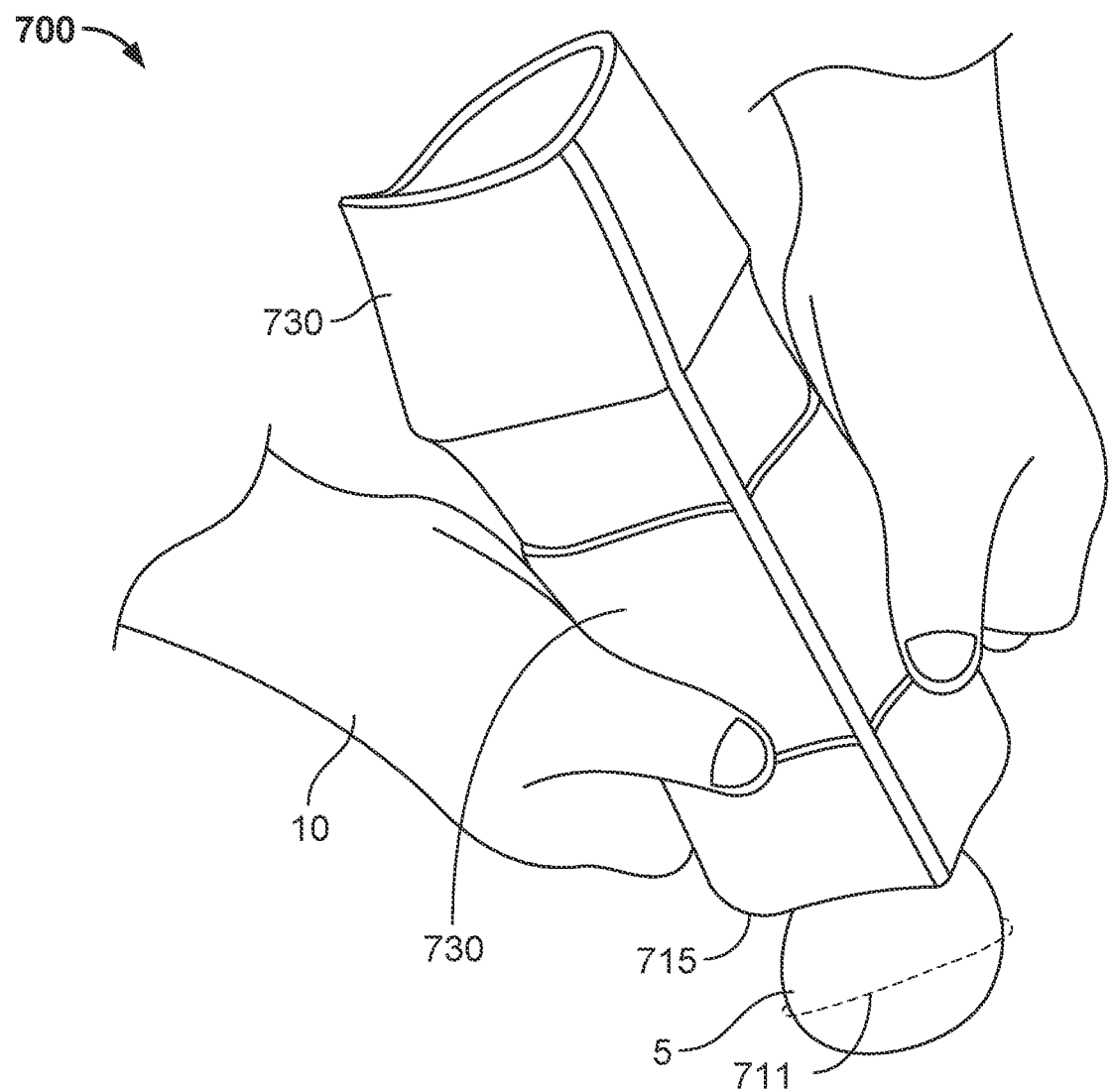
FIG. 7B shows the surgical delivery device portion of FIG. 7A in use.

Referring to FIGS. 7A-7B, an example surgical delivery device portion 700 is shown in a first, planar configuration (FIG. 7A) and a second, expanded configuration (FIG. 7B). In various example embodiments, surgical delivery device 700 includes one or more features as described herein with reference to surgical delivery device 100, 200, 400, 500, 600.

Referring to FIG. 7A, surgical delivery device 700 has a rectangular-shaped body section expandable into a cylindrical shape. Surgical delivery device 700 has equal-sized openings at ends 729a, 729b, and can be used to deliver an implant without substantially deforming or compressing the implant as it is delivered from surgical delivery device 700.

Referring to FIG. 7B, an example delivery operation using surgical delivery device 700 is shown. In an example embodiment, the delivery operation includes dispensing implant 5 through the delivery opening 715. The user 10 can gently manipulate implant 5 through the walls of surgical delivery device 700, causing the implant to be dispensed into surgical opening 711. In an example embodiment, surgical delivery device 700 is not tapered and/or delivery opening 715 is sufficiently larger (e.g., larger than implant 5) such that implant 5 is not compressed during delivery from delivery opening 716.

User 10 can manipulate and/or push implant 5 through walls of surgical delivery device 700. In some embodiments, a user may grasp handles 730 with one or both hands during delivery to facilitate manipulation of implant 5 and/or advance implant 5 through delivery opening 715. Surgical delivery device 700 facilitates delivery of implant 5 without direct contact of implant 5 by the user. In some embodiments, the user can elect to contact implant 5 during delivery, such as by using a properly sterilized hand, glove, instrument, etc.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A surgical implant delivery device to provide one or more flexible sleeves for delivery of at least one silicone implant, comprising:
a flexible main body that is flat and adjustable to an expanded condition to provide an interior cavity sized to receive a silicone implant, the flexible main body comprising an intermediate section, a first tapered section adjacent to the intermediate section and offset from a central lateral axis of the intermediate section, and a second tapered section adjacent to the intermediate section and offset from the central lateral axis of the intermediate section opposite from the first tapered section so that at least one of the first and second tapered sections is separable from a portion of the intermediate section for expansion to a tapered implant guide sleeve, wherein the first tapered section extends away from the intermediate section to a first end that extends parallel to the central lateral axis, and the second tapered section extends away from the intermediate section to a second end that extends parallel to the central lateral axis and the first end; and
first and second exterior handles attached to opposing major surfaces of the flexible main body at a location proximate to a first cut line formed on the flexible main body to provide grasping locations when expanding at least one of said first and second tapered sections into said tapered implant guide sleeve.

2. The surgical implant delivery device of claim 1, wherein the flexible main body comprises a pair of equally shaped planar polymer sheets attached together along at least a majority portion of their peripheries.

3. The surgical implant delivery device of claim 1, wherein the flexible main body is non-symmetric about a central longitudinal axis of the intermediate section extending perpendicular to the central lateral axis and in a longitudinal direction from the first tapered section to the second tapered section.

4. The surgical implant delivery device of claim 3, wherein the first end of the first tapered section is laterally spaced apart from the central longitudinal axis on a first side lateral side of the longitudinal axis, and the second end of the second tapered section is laterally spaced apart from the central longitudinal axis on a second side lateral side opposite from the first lateral side.

5. The surgical implant delivery device of claim 4, wherein the first end of the first tapered section defines a first opening and the second end of the second tapered section defines a second opening equally sized with the first opening.

6. The surgical implant delivery device of claim 4, wherein the first end of the first tapered section and the second end of the second tapered section are sealed.

7. The surgical implant delivery device of claim 1, wherein the first cut line is a first intermediate cut line formed on the flexible main body and positioned at a first end of the intermediate section adjacent the first tapered section.

8. The surgical implant delivery device of claim 7, further comprising: a second intermediate cut line formed on the flexible main body and positioned at a second end of the intermediate section adjacent the second tapered section, and a third intermediate cut line formed on the flexible main body and positioned along the central lateral axis of the intermediate section midway between the first tapered section and the second tapered section.

9. The surgical implant delivery device of claim 1, further comprising: a first tip cut line formed on the main body proximate to the first end of the first tapered section so as to a define predetermined opening size when the first tapered section defines said tapered implant guide sleeve, and a second tip cut line formed on the main body proximate to the second end of the second tapered section so as to define the predetermined opening size when the second tapered section defines said tapered implant guide sleeve.

10. The surgical implant delivery device of claim 1, wherein the first and second tapered sections are separable from the intermediate section and expandable to define tapered implant guide sleeve for delivery of first and second silicone implants to first and second targeted pockets.

11. The surgical implant delivery device of claim 1, wherein the intermediate section is separable from the first and second tapered sections and expandable to define a cylindrical implant guide sleeve for delivery of the silicone implant to a targeted pocket.

12. The surgical implant delivery device of claim 1, wherein the flexible main body comprises a transparent window positioned between opaque wall regions such that the interior cavity of the main body is viewable through the transparent window.

13. The surgical implant delivery device of claim 12, wherein the transparent window is shaped as a transparent strip extending entirely from the first end to the second end.

14. The surgical implant delivery device of claim 1, further comprising an antimicrobial material positioned in the interior cavity of the flexible main body.

15. The surgical implant delivery device of claim 1, wherein the flexible main body is non-symmetric about the central lateral axis of the rectangular section positioned midway between the first tapered section and the second tapered section and parallel to the first and second ends.

16. The surgical implant delivery device of claim 1, wherein the intermediate section comprises a first lateral edge and a second lateral edge opposite from the first lateral edge, the first and second lateral edges extending parallel to a central longitudinal axis of the intermediate section.

17. The surgical implant delivery device of claim 16, wherein the first tapered section comprises a first tapered edge extending from the first lateral edge toward the first end at a first taper angle of about 150-degrees, and the second tapered section comprises a second tapered edge extending from the second lateral edge toward the second end at a second taper angle of about 150-degrees.

18. The surgical implant delivery device of claim 17, the first tapered section comprises a first straight edge collinear with the second lateral edge of the intermediate section and extending toward the first end, and the second tapered section comprises a second straight edge collinear with the first lateral edge of the intermediate section and extending toward the second end equally sized with the first end.

* * * * *